United States Patent
Moffitt

(10) Patent No.: US 9,604,058 B2
(45) Date of Patent: Mar. 28, 2017

(54) METHOD FOR ACHIEVING LOW-BACK SPINAL CORD STIMULATION WITHOUT SIGNIFICANT SIDE-EFFECTS

(71) Applicant: BOSTON SCIENTIFIC NEUROMODULATION CORPORATION, Valencia, CA (US)

(72) Inventor: Michael A. Moffitt, Valenca, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 786 days.

(21) Appl. No.: 13/855,589

(22) Filed: Apr. 2, 2013

(65) Prior Publication Data

US 2013/0268021 A1 Oct. 10, 2013

Related U.S. Application Data

(60) Provisional application No. 61/621,331, filed on Apr. 6, 2012.

(51) Int. Cl.
*A61N 1/36* (2006.01)
*A61N 1/05* (2006.01)

(52) U.S. Cl.
CPC ........ *A61N 1/36071* (2013.01); *A61N 1/0551* (2013.01); *A61N 1/36182* (2013.01)

(58) Field of Classification Search
USPC .................................................. 607/46, 117
See application file for complete search history.

(56) References Cited

U.S. PATENT DOCUMENTS

| | | | |
|---|---|---|---|
| 6,421,566 B1 * | 7/2002 | Holsheimer | 607/46 |
| 7,650,184 B2 | 1/2010 | Walter | |
| 7,742,810 B2 | 6/2010 | Moffitt et al. | |
| 8,019,439 B2 | 9/2011 | Kuzma et al. | |
| 2007/0142863 A1 | 6/2007 | Bradley | |
| 2007/0150036 A1 | 6/2007 | Anderson | |
| 2007/0168004 A1 | 7/2007 | Walter | |
| 2007/0168007 A1 | 7/2007 | Kuzma et al. | |
| 2008/0294226 A1 | 11/2008 | Moffitt et al. | |
| 2010/0030300 A1 * | 2/2010 | Feler et al. | 607/46 |
| 2011/0009923 A1 | 1/2011 | Lee | |

* cited by examiner

*Primary Examiner* — Paula J Stice
(74) *Attorney, Agent, or Firm* — Lowe Graham Jones PLLC; Bruce E. Black

(57) ABSTRACT

A method for treating an ailment of a patient using at least one electrode implanted within a spinal column of the patient at a T4-T6 spinal nerve level. The method comprises increasing an activation threshold of a side-effect exhibiting neural structure relative to the activation threshold of a dorsal column (DC) nerve fiber of the patient, and applying electrical stimulation energy to the DC nerve fiber via the at least one electrode while the activation threshold of the neural structure is increased, thereby treating the ailment while minimizing stimulation of the neural structure. Another method comprises applying electrical stimulation energy to the spinal column of the patient via the plurality of electrodes, thereby generating a medio-lateral electrical field relative to the spinal column of the patient and treating the ailment.

15 Claims, 7 Drawing Sheets

METHOD FOR ACHIEVING LOW-BACK SPINAL CORD STIMULATION WITHOUT SIGNIFICANT SIDE-EFFECTS

RELATED APPLICATION DATA

The present application claims the benefit under 35 U.S.C. §119 to U.S. provisional patent application Ser. No. 61/621,331, filed Apr. 6, 2012. The foregoing application is hereby incorporated by reference into the present application in its entirety.

FIELD OF THE INVENTION

Embodiments of the present disclosure relate generally to tissue stimulation systems. In particular, embodiments of the instant disclosure relate to spinal cord stimulation.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis. Deep Brain Stimulation (DBS) has also been applied therapeutically for well over a decade for the treatment of refractory chronic pain syndromes, and DBS has recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. In addition, Functional Electrical Stimulation (FES) systems, such as the Freehand system by NeuroControl (Cleveland, Ohio) have been applied to restore some functionality to paralyzed extremities in spinal cord injury patients.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient. The neurostimulation system may further comprise a handheld patient programmer in the form of a remote control (RC) to instruct the neurostimulator to generate electrical stimulation pulses in accordance with selected stimulation parameters. A clinician, for example, may program the RC by using a computerized programming system referred to as a clinician's programmer (CP), which typically includes a general purpose computer, such as a laptop, with a programming software package installed thereon.

In the context of an SCS procedure, one or more neurostimulation leads are introduced through the patient's back into the epidural space, such that the electrodes carried by the leads are arranged in a desired pattern and spacing to create an electrode array. Multi-lead configurations have been increasingly used in electrical stimulation applications (e.g., neurostimulation, cardiac resynchronization therapy, etc.). In the neurostimulation application of SCS, the use of multiple leads increases the stimulation area and penetration depth (therefore coverage), as well as enables more combinations of anodic and cathodic electrodes for stimulation, such as transverse multipolar (bipolar, tripolar, or quadrapolar) stimulation, in addition to any longitudinal single lead configuration. After proper placement of the neurostimulation leads at the target area of the spinal cord, the leads are anchored in place at an exit site to prevent movement of the neurostimulation leads. To facilitate the location of the neurostimulator away from the exit point of the neurostimulation leads, lead extensions are sometimes used.

The neurostimulation leads, or the lead extensions, are then connected to the IPG, which can then be operated to generate electrical pulses that are delivered, through the electrodes, to the targeted spinal cord tissue. The stimulation creates the sensation known as paresthesia, which can be characterized as an alternative sensation that replaces the pain signals sensed by the patient.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment).

To aid the patient care professional in correlating the paresthesia experienced by the patient during stimulation and the dermatomes corresponding the region or regions of pain experienced by the patient, computer programming systems typically include dermatome maps of the human body onto which regions of pain and regions of paresthesia experienced by the patient can be recorded to allow the patient care professional to determine the effectiveness of the therapy. Each dermatome corresponds to a region of the body that is mainly supplied by a single spinal nerve (i.e., a dorsal root (DR) nerve). In each patient, there are eight cervical spinal nerves designated C1-C8, twelve thoracic spinal nerves designated T1-T12, five lumbar spinal nerves designated L1-L5, and five sacral spinal nerves designated S1-S5.

It is believed that large diameter dorsal column (DC) nerve fibers, which extend rostro-caudally along the spinal cord and interact with the DR nerves via the dorsal horn, are the major targets for SCS for overlaying the patient's painful regions with paresthesia. It can then be appreciated that the clinical goal of pain relief can often be achieved by placing the electrodes of the stimulation lead(s) as near as possible to the innervating DC nerve fibers associated with the dermatomic area of pain, and if necessary, "tuning" the electrical stimulation by adjusting one or more stimulation parameters. In some cases, this is relatively simple due to the relatively close proximity of the active stimulating electrodes to the innervating DC nerve fibers, as well as the size and/or orientation of the stimulating electrodes relative to these DC nerve fibers.

However, in some applications of SCS, due to the thickness of the cerebral spinal fluid (CSF) along certain portions of the spinal canal, it is difficult to stimulate DC nerve fibers without also stimulating nearby DR nerve fibers, which may cause discomfort to the patient in the regions in which the DR nerve fibers innervate. This phenomenon can best be appreciated in the context of treating lower back via SCS, where it is very difficult to provide paresthesia to the lower back of a patient without causing uncomfortable chest/abdominal wall sensations due to the stimulation of innervating DR nerve fibers.

For example, with reference to the empirical evidence illustrated in the graphs of FIG. 1, although the maximum probability of achieving paresthesia in the lower back of a patient (approximately 40%) occurs when the T5 spinal level is stimulated as shown in chart 1, the probability of creating side-effects in the form of stimulation of the abdomen (approximately 80%) also occurs when the T5 spinal level is stimulated as shown in chart 2. This phenomenon is mainly due to the fact that as the cerebrospinal fluid (CSF) layer becomes thicker, it becomes more difficult to stimulate DC nerve fibers without also stimulating DR nerve fibers. As shown in chart 3, the maximum thickness of the CSF layer occurs at the T5 spinal level, thereby causing the maximum probability of uncomfortable abdominal stimulation to track the maximum probability of achieving lower back paresthesia.

As a result, clinicians have traded off ineffective stimulation for patient comfort by stimulating the DC nerve fibers well outside of the optimum spinal level range of T4-T6 (shown by band 4), and in particular, well above the T6 spinal level where the probability of achieving lower back paresthesia precipitously drops off. For example, the historical spinal level target for achieving lower back paresthesia is in the T9-T10 range (shown by band 5). Uncomfortable stimulation of the abdomen can be minimized by locating the lead or leads along the centerline of the spinal cord in order to preferentially stimulate the DC nerve fibers over the DR nerve fibers. However, in this case, the probability of achieving lower back paresthesia drops down to the 15-20% range, while the probability of causing uncomfortable abdominal stimulation is still in the 40-55% range. More recently, lower back paresthesia with minimal side effects has been achieved in the T7-T8 range using current steering techniques to refine the resulting electrical field (shown by band 6). In this case, the probability achieving lower back paresthesia is in the 20-30% range.

Because it is difficult to achieve lower back paresthesia without uncomfortable abdominal stimulation, treatment of chronic low back pain via SCS is conventionally treated only ancillary to the treatment of some other ailment, such as chronic leg pain. That is, the lead or leads are implanted in the patient for treating a particular ailment, and if the effective lower back paresthesia can be obtained without significant side effects, than the lower back pain is treated along with the particular ailment.

There, thus, remains a need to provide an SCS regimen that provides relief for chronic lower back pain while minimizing the probability of side effects. The art remains unable to apply SCS in the most beneficial location. There remains a need for an SCS technique that would allow positioning of SCS leads in the optimal therapeutic location for lower back DC stimulation without undesirable collateral effects of stimulating DR nerve fibers.

SUMMARY OF THE INVENTION

In accordance with one aspect of the present inventions, a method for treating an ailment (e.g., lower back pain) of a patient using at least one electrode implanted within a spinal column of the patient at a T4-T6 spinal nerve level is provided. The method comprises increasing an activation threshold of a side-effect exhibiting neural structure (e.g., a dorsal root (DR) nerve fiber) relative to the activation threshold of a dorsal column (DC) nerve fiber of the patient, and applying electrical stimulation energy to the DC nerve fiber via the at least one electrode while the activation threshold of the neural structure is increased, thereby treating the ailment while minimizing (and preferably preventing) stimulation of the neural structure.

The activation threshold of the neural structure relative to the activation threshold of the DC nerve fiber may be increased by applying electrical suppression energy to the neural structure. For example, the electrical stimulation energy may be applied to DC nerve fiber by sinking electrical current at a first electrode adjacent the DC nerve fiber, thereby treating the chronic pain, and the electrical suppression energy can be applied to the neural structure by sourcing at least a portion of the electrical current from a second electrode adjacent the neural structure, thereby increasing the activation threshold of the neural structure. At least a portion of the electrical current sourced at the second electrode may be sunk into a remote electrode.

The electrical suppression energy may also be applied to another neural structure (e.g., a second DR nerve fiber) adjacent the DC nerve fiber to increase the activation threshold of the other neural structure by sourcing at least another portion of the electrical current from a third electrode adjacent the other neural structure, in which case, the electrical stimulation energy may be applied to the DC nerve fiber of the patient while the activation threshold of the other neural structure is increased, thereby treating the chronic pain while minimizing stimulation of the other neural structure. In this case, the first electrode may be a center electrode, and the second and third electrodes may be flanking electrodes of a tripole configuration located between the neural structures.

The activation threshold of the neural structure may alternatively be increased by applying a sub-threshold, hyperpolarizing conditioning pre-pulse (e.g., one having a duration less than 200 µs) to the neural structure, and the electrical stimulation energy may be applied to the DC nerve fiber by applying a depolarizing stimulation pulse to the DC nerve fiber.

The activation threshold of the neural structure may alternatively be increased by applying electrical background energy to the neural structure in accordance with at least one stochastic parameter to the neural structure. In one method, the stochastic parameter(s) comprises at least one of an interpulse interval, pulse amplitude, pulse shape, and pulse duration. In another method, the electrical background energy may comprise white noise, in which case, the stochastic parameter may comprise a frequency.

In accordance with another aspect of the present invention, another method for treating an ailment (e.g., lower back pain) of a patient using at least one electrode implanted within a spinal column of the patient at a T4-T6 spinal nerve level is provided. The method comprises applying electrical stimulation energy to the spinal column of the patient via the plurality of electrodes, thereby generating a medio-lateral electrical field relative to the spinal column of the patient and treating the ailment. The medio-lateral electrical field may increase an activation threshold of a dorsal root (DR) nerve fiber relative to the activation threshold of a dorsal column (DC) nerve fiber of the patient. The medio-lateral field may be generated by sinking electrical current at a first one of the electrodes adjacent the DC nerve fiber, thereby treating the ailment, and sourcing at least a portion of the electrical current from a second one of the electrodes adjacent the DR nerve fiber, thereby increasing the activation threshold of the neural structure. The medio-lateral electrical field may also increase an activation threshold of another DR nerve fiber relative to the activation threshold of DC nerve fiber by sourcing at least another portion of the electrical current from a third one of the electrodes adjacent the other DR nerve fiber. The first electrode may be a center electrode, and the second and third electrodes may be flanking electrodes of a tripole configuration located between the DR nerve fibers.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DESCRIPTION OF THE EMBODIMENTS

Figure 2:
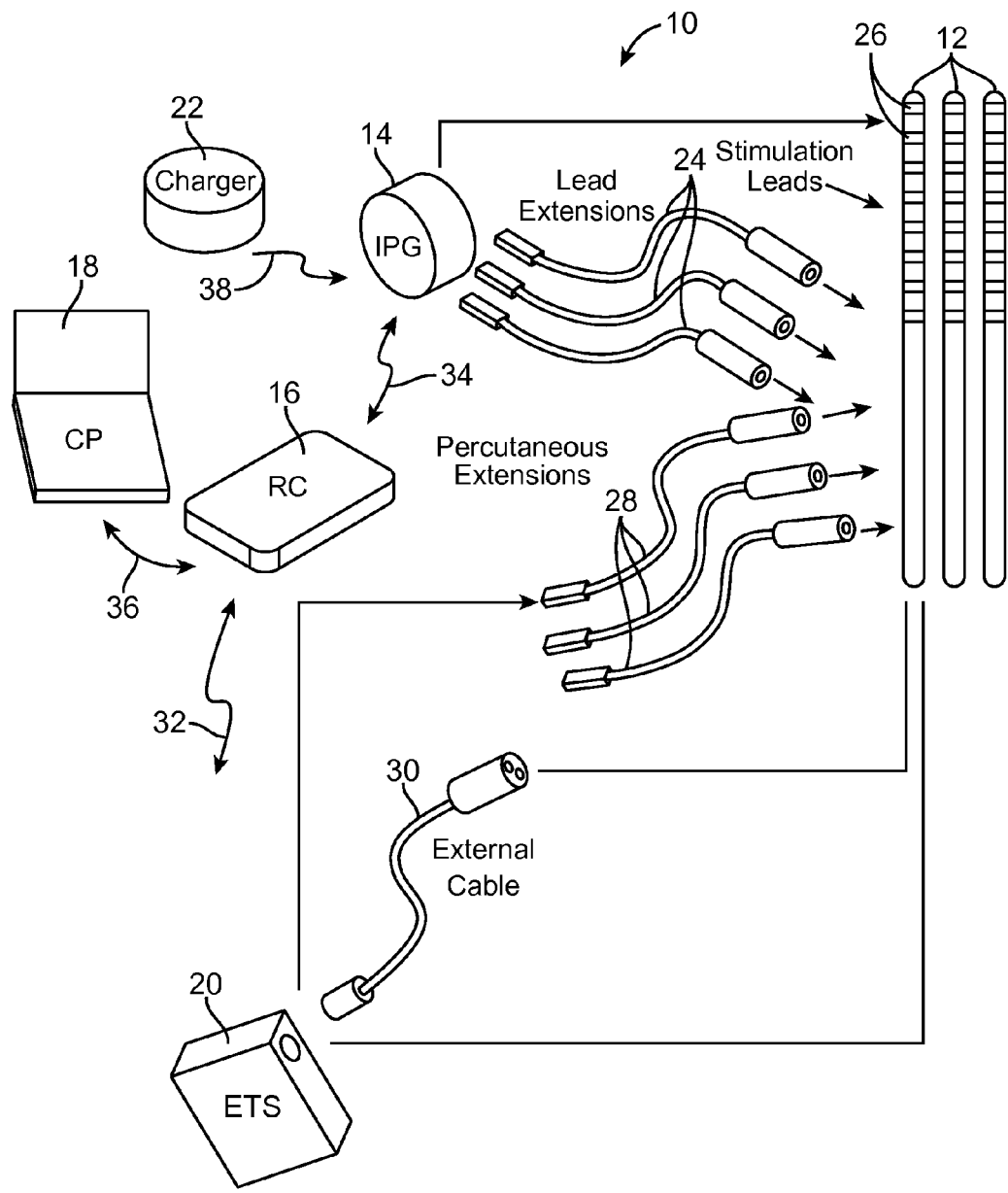
FIG. 2 is a plan view of a Spinal Cord Stimulation (SCS) system constructed in accordance with one embodiment of the present inventions.

Turning first to FIG. 2, an exemplary SCS system 10 generally comprises a plurality of stimulation leads 12 (in this case, three), an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 2, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 1:
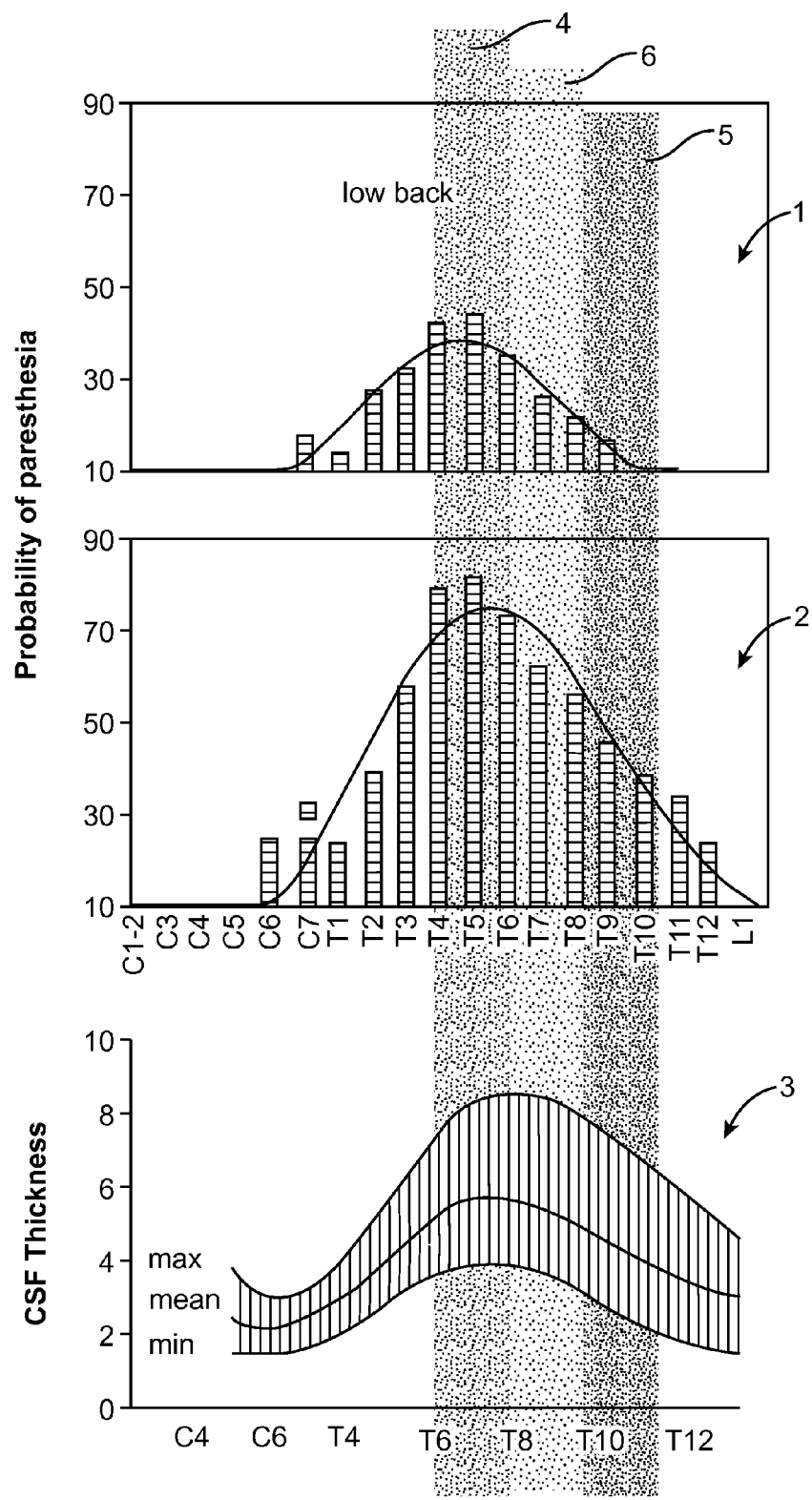
FIG. 1 is a graph of empirical evidence showing the probability of achieving paresthesia and the probability of creating side-effects as a function of spinal nerve level.
Figure 3:
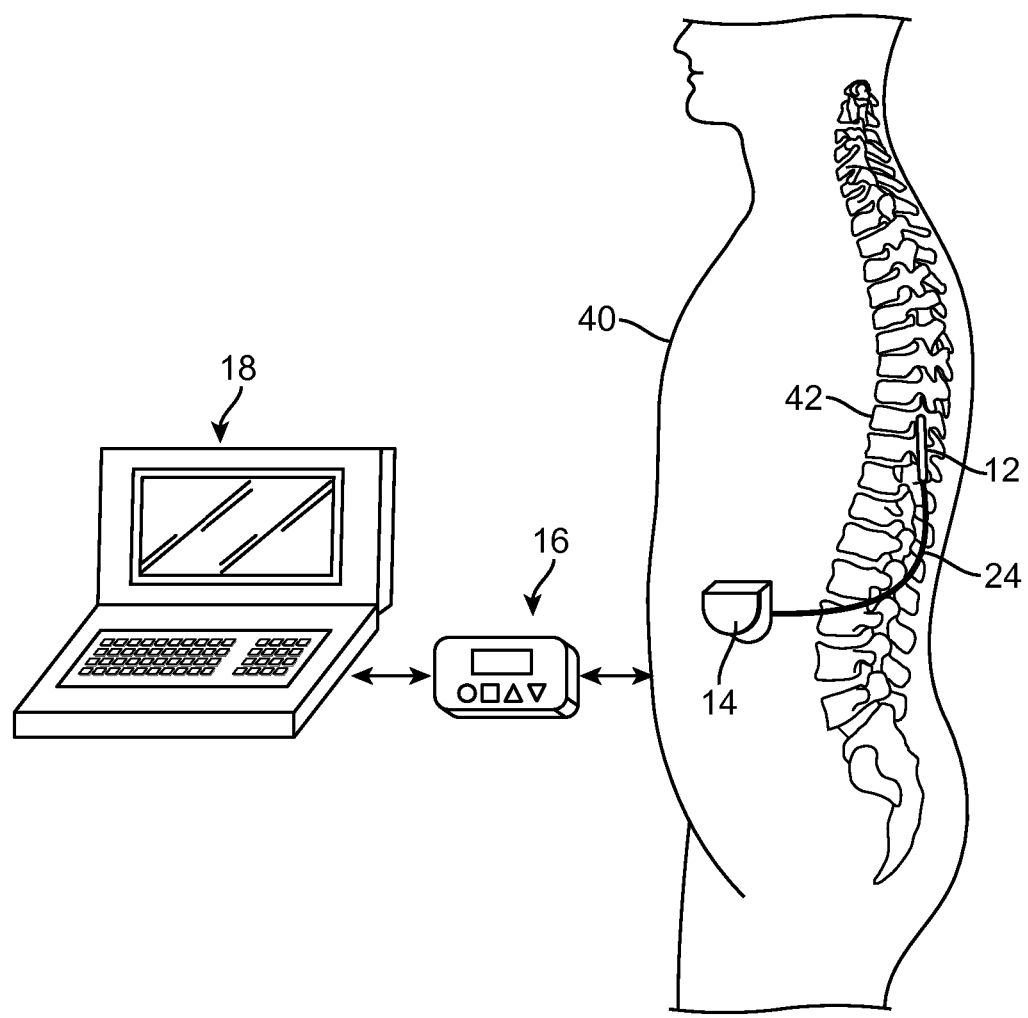
FIG. 3 is a plan view of the SCS system of FIG. 2 in use within a patient.

As shown in FIG. 3, the stimulation leads 12 are implanted within the spinal column 42 of a patient 40. The preferred placement of the electrode leads 12 is adjacent, i.e., resting near, the spinal cord area to be stimulated. The stimulation leads 12 are preferably implanted in the T4-T6 spinal nerve range. That placement achieves maximum DC stimulation, as shown in band 4 of FIG. 1. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 4:
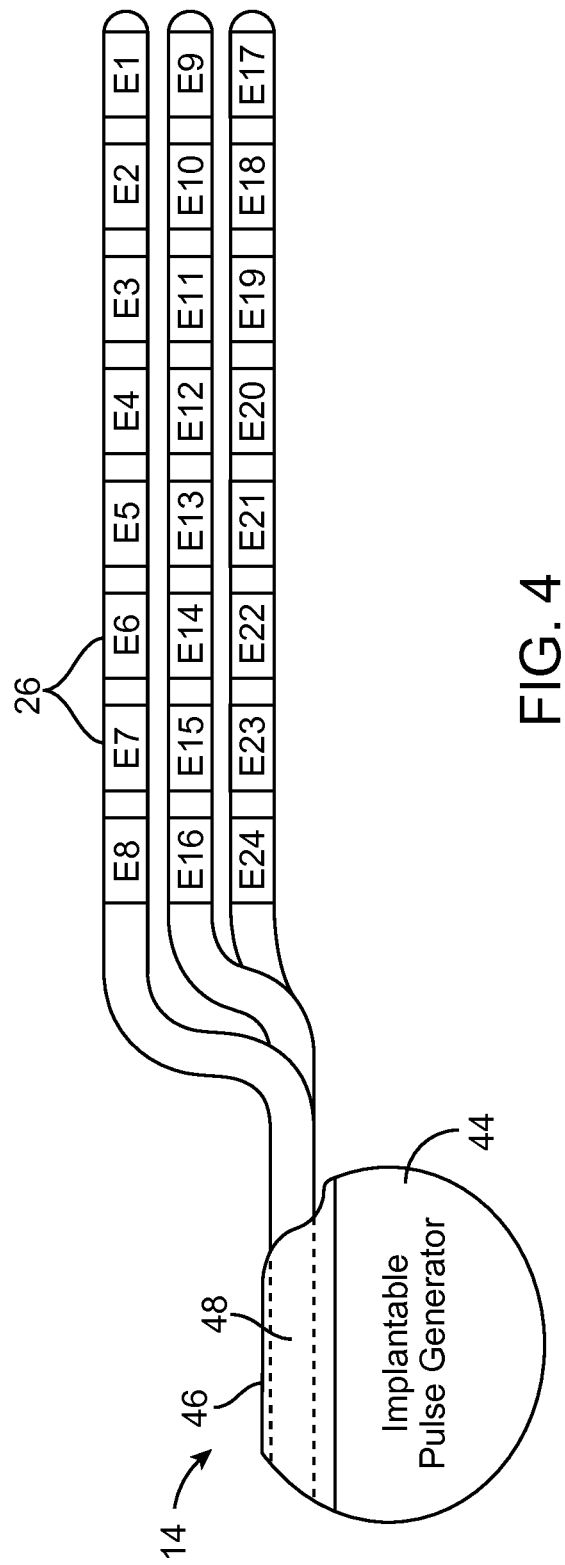
FIG. 4 is a plan view of an implantable pulse generator (IPG) and three percutaneous stimulation leads used in the SCS system of FIG. 2.

Referring now to FIG. 4, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application.

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 5:
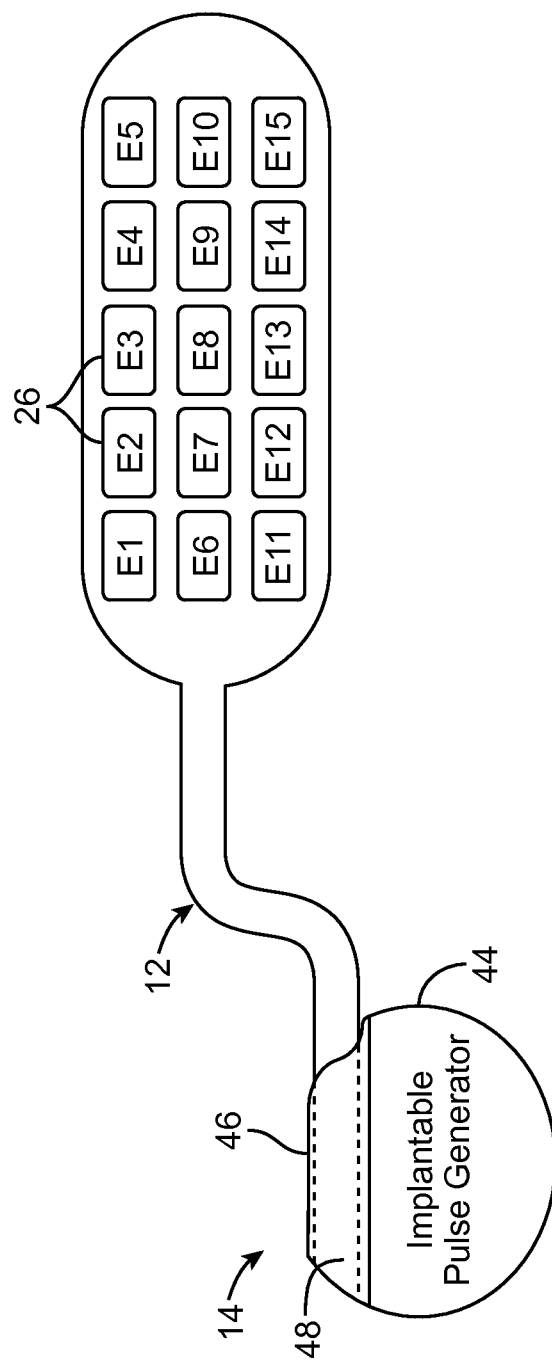
FIG. 5 is a plan view of an implantable pulse generator (IPG) and a surgical paddle lead used in the SCS system of FIG. 2.

Alternatively, as illustrated in FIG. 5, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 4 and 5, the IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes one or more ports (three ports 44 or three percutaneous leads or one port for the surgical paddle lead) for receiving the proximal end(s) of the stimulation lead(s) 12. In the case where the lead extensions 24 are used, the port(s) 44 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and the case 40. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 6:
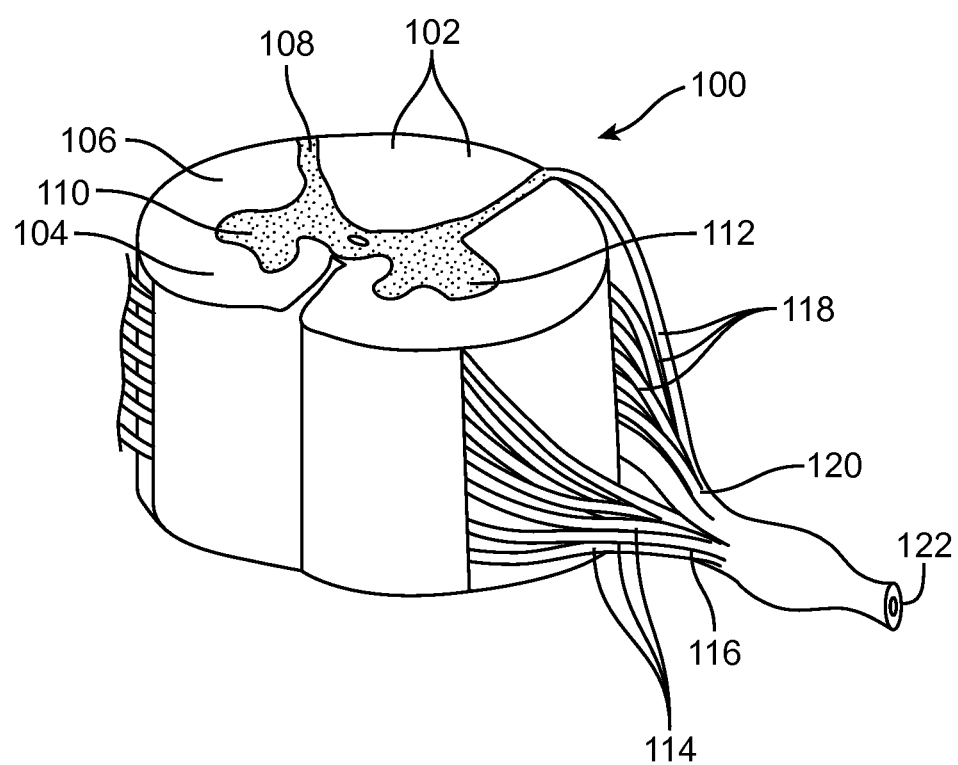
FIG. 6 is a peripheral view of the spinal cord and spinal nerves.
Figure 7:
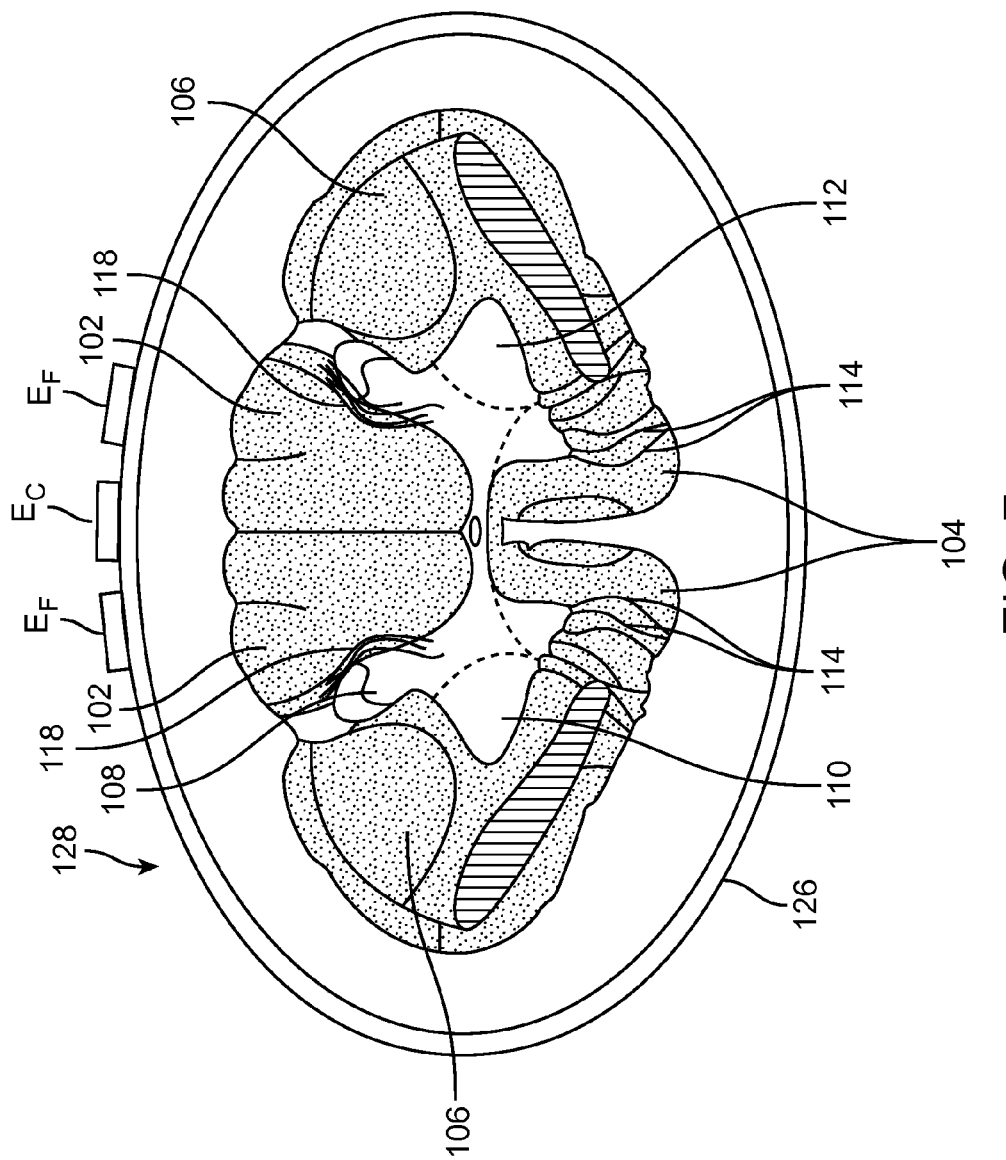
FIG. 7 is a cross-sectional view showing one electrode arrangement relative to the spinal cord.

Referring now to FIGS. 6 and 7, the portions of the spinal cord 100 that are relevant to the present inventions will be described. The spinal cord 100 is divided into three functional columns: the dorsal column 102, the ventral column 104, and the lateral columns 106. Similarly, the butterfly-shaped gray matter of the spinal cord 100 is divided into the dorsal horn 108, the ventral horn 110, and the lateral horn 112.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5. The spinal cord 100 is enclosed by a dura mater 126, with an epidural space 128 surrounding the dura mater 126.

In conventional SCS techniques, stimulation is applied to the dorsal column 102 of the spinal cord 100 at a spinal nerve level greater than T6 to treat chronic neuropathic pain, and accordingly, stimulation leads are positioned in the dorsal region of the epidural space 128, such that the stimulating electrodes 26 are located above the T6 spinal nerve level. As opposed to the conventional SCS techniques, the methods of the present invention position the stimulation leads in the dorsal region of the epidural space 128, such that the stimulating electrodes 26 are located in the range of the T4-T6 spinal nerve levels.

During application of the stimulation energy to the dorsal column 102, the activation threshold of neural structures (e.g., the DR nerve fibers 118) relative to the activation threshold of the dorsal column 102 is preferably increased, so that the neural structures are not inadvertently stimulated. As will be described in further detail below, different techniques can be used to increase the activation thresholds of these neural structures relative to the activation threshold of the dorsal column 102.

Referring to FIG. 7, a configuration of three electrodes (labeled $E_C$ for the center electrode, and $E_F$ for the flanking electrodes) may be arranged relative to a pair of adjacent DR nerve fiber groupings 116, such that it is aligned along the longitudinal axis of the spinal cord 100 (i.e., in the rostro-caudal direction) between the DR nerve groupings 118, such that the flanking electrodes $E_F$ of the tripole configuration are respectively closest to the DR nerve fiber groupings 118. The electrode configurations can be formed, e.g., using any row of electrodes 26 on three side-by-side percutaneous leads 12 (shown in FIG. 4) or any row of electrodes 26 on the surgical paddle lead 12 (shown in FIG. 5).

As briefly discussed above, the electrodes 26 may be configured in a manner that increases the activation threshold of the DR nerve fiber groupings 118 relative to the activation threshold of the dorsal column 102 in order to inhibit the stimulation of DR nerve fiber groupings 118 when the dorsal column 102 is stimulated.

The techniques described below apply electrical suppression energy to the DR nerve fiber groupings 118 to increase their activation threshold. Preferably, the electrodes 26 are placed as closely as possible to the spinal cord 100 in order to maximize the resolution of the energy transmitted by the electrodes 26; that is, to focus the stimulating effect of the stimulation energy on a target site in the dorsal column 102, and to focus the activation-threshold-increasing effect of the suppression energy on the DR nerve fiber groupings 118. Preferably, the proximity of the electrodes 26 to the spinal cord 100 should be less than one-half of the distance between adjacent electrodes 26 to ensure proper resolution.

In one technique for preventing inadvertent stimulation of the DR nerve fiber groupings 118, the electrodes are configured as a tripole, such that the flanking electrodes $E_F$ adjacent the two DR nerve fiber groupings 118 are anodes, and the center electrode $E_C$ is a cathode. In this configuration, electrical stimulation energy conveyed between the cathode(s) and anode(s) creates a medio-lateral electrical field that stimulates the dorsal column 102, while preventing stimulation of the DR nerve fiber groupings 118. That is, the electrical current sourced by the outer flanking electrodes $E_F$ hyperpolarizes the DR nerve fiber groupings 118, thereby increasing their activation threshold, while the electrical current sunk by the center electrode $E_C$ depolarizes the nerve fibers in the dorsal column 102, thereby creating a locus of stimulation that is confined to the region of the dorsal column 102 adjacent the center electrode $E_C$. In effect, the center electrode $E_C$ generates the electrical stimulation energy at the dorsal column 102, while the flanking electrodes $E_F$ "push" the electrical stimulation energy away from the DR nerve fiber groupings 118.

It is desirable that the locus of stimulation be as narrow as possible without having to increase its depth necessarily, thereby stimulating target nerve fibers within the dorsal column 102, while preventing stimulation of the DR nerve fiber groupings 118. This would require an increase in the electrical current sourced at the flanking electrodes $E_F$. However, this necessarily may result in an increase in the current sunk by the center electrode $E_C$, thereby increasing the depth of the locus of stimulation, which may lead to undesirable outcomes (e.g., discomfort or undesirable motor activity). As such, a portion of the electrical current sourced at the flanking electrodes $E_F$ can be additionally sunk at a remote electrode (e.g., the case or even a therapeutic electrode remote from the tripole configuration), thereby creating a local current imbalance at the target site of the dorsal column 102.

Further details discussing the use of tripolar electrode arrangements to render tissue less excitable to subsequent stimulation are disclosed in U.S. patent application Ser. No. 11/300,963, entitled "Apparatus and Methods for Stimulating Tissue," which is expressly incorporated herein by reference.

In another technique for preventing inadvertent stimulation of the DR nerve fiber groupings 118, a sub-threshold, hyperpolarizing conditioning pre-pulse can be applied by flanking electrodes $E_F$ to the adjacent DR nerve fiber groupings 118, and a depolarizing stimulation pulse can be subsequently applied by the center electrode $E_C$ to the dorsal column 102. The duration between the conditioning pulse and the stimulation pulse is preferably zero, but at the least should be less than 100 μs, and more preferably, less than 30 μs. The conditioning pre-pulse preferably has a relatively short duration, preferably less than 200 μs, more preferably less than 150 μs, and most preferably less than 75 μs, such that m-gates of the sodium ion channels in the neural axons are closed to render the tissue less excitable to subsequent stimulation. The stimulation pulse preferably has a relatively short duration, e.g., less than 200 μs.

Optionally, a relatively long depolarizing conditioning pulse preceding the relatively short hyperpolarizing conditioning pulse can be applied by the flanking electrodes $E_F$, such that h-gates of the sodium ion channels in the neural axons are closed to render the tissue even less excitable to subsequent stimulation. To determine the optimum amplitude for the conditioning pre-pulse(s), the amplitude level of the stimulation pulse may be incrementally increased until a side-effect is experienced by the patient, and for each incremental increase in the stimulation pulse, the amplitude of the conditioning pre-pulse(s) may be increased until the side-effect is eliminated or minimized.

Further details discussing the use of conditioning pre-pulses to render tissue less excitable to subsequent stimulation are disclosed in U.S. patent application Ser. No. 11/752,895, entitled "Short Duration Pre-Pulsing to Reduce Stimulation-Evoked Side-Effects," which is expressly incorporated herein by reference.

In still another technique for preventing inadvertent stimulation of the DR nerve fiber groupings 118, electrical background energy is conveyed from the flanking electrodes $E_F$ in accordance with at least one stochastic parameter. If the electrical background energy is in the form of pulses, the stochastic parameter may comprise at least one of an inter-pulse interval, pulse amplitude, pulse shape, and pulse duration. If the electrical background energy is white noise, the stochastic parameter may be a frequency.

The three electrodes can be configured as stimulating electrodes in a tripolar arrangement (center electrode $E_C$ as the cathode, and flanking electrodes $E_F$ as the anodes) in a manner described above, while the flanking electrodes $E_F$ can be configured as background electrodes in a monopolar arrangement with the IPG case 44. Thus, electrical stimulation energy is conveyed between the tripolar arrangement of the electrodes, thereby therapeutically stimulating the dorsal column 102, and electrical background energy is conveyed between the flanking electrodes $E_F$ and the IPG case 44, thereby decreasing the excitability of the DR nerve fiber groupings 118.

Notably, due to the monopolar arrangement, the field strength of the electrical background energy conveyed from the flanking electrodes $E_F$ decays at a relatively low rate with distance. As such, the flanking electrodes $E_F$ may be relatively far from the DR nerve fiber groupings 118 for them to modulate the excitability of the DR nerve fiber groupings 118. Alternatively, the electrical background energy may be conveyed from flanking electrodes $E_F$ in bipolar arrangement. However, in this case, due to current shunting, the flanking electrodes $E_F$ must be relatively close to the DR nerve fiber groupings 118. In either case, as a general rule, the excitability of the DR nerve fiber groupings 118 will be decreased if the magnitude of the electrical background energy is relatively high. Alternatively, electrical background energy with a relatively low magnitude may be conveyed from the center electrode $E_C$, thereby increasing the excitability of the dorsal column 102. In effect, the activation threshold of the DR nerve fiber groupings 118 will be increased relative to the activation threshold of the dorsal column 102 by decreasing the activation threshold of the dorsal column 102.

Because the excitability of the DR nerve fiber groupings 118 will be decreased by the electrical background energy, the effect that the inadvertent conveyance of the electrical stimulation energy to the DR nerve fiber groupings 118 will be decreased. In one method, the electrical background energy is set equal to or higher than 10% of the perception threshold of the patient. Preferably, the electrical background energy is sub-threshold (i.e., does not stimulate nerve fibers), but may be supra-threshold if it provides therapy to the patient or can otherwise be tolerated by the patient. Ultimately, the magnitudes of the electrical stimulation energy and electrical background energy can be set relative to each other through trial and error.

Further details discussing the use of electrical background energy to render tissue less excitable to subsequent stimulation are disclosed in U.S. patent application Ser. No. 12/501,127, entitled "System and Method for Reducing Excitability of Dorsal Root Fiber by Introducing Stochastic Background Noise," which is expressly incorporated herein by reference.

In an optional embodiment, a set of sensors, such as sense amplifiers, accelerometers, chemical sensors, or thermal sensors, may be employed to ensure that the stimulation applied is efficacious, as well as to identify side effects arising from stimulation activity. For example, a sense amplifier coupled to the electrodes 26 may detect dorsal root activity and subsequently, the stimulation output may be altered to reduce dorsal root activity.

It should be understood that the SCS system 10 may be utilized alone or in conjunction with other known implantable devices, such as vagal stimulators, pacemakers, defibrillators, sympathetic chain stimulators, brain stimulators, and so on. The SCS system 10 may interact with other stimulator systems, and in one embodiment, all the stimulator systems may be contained within a single system. In such embodiments, the stimulation source and mechanism to control and/or modify stimulation may be applied through a common source. For example, the SCS system 10 may have multiple leads enabling multiple purposes, e.g., an additional stimulation lead or leads positioned over the dorsal column to provide conventional stimulation.

Although particular embodiments of the present disclosure have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating an ailment of a patient using at least one electrode implanted within a spinal column of the patient, the method comprising:
   increasing an activation threshold of a side-effect exhibiting neural structure relative to the activation threshold of a dorsal column (DC) nerve fiber of the patient; and
   applying electrical stimulation energy to the DC nerve fiber via the at least one electrode while the activation threshold of the neural structure is increased, thereby treating the ailment while minimizing stimulation of the neural structure, wherein the at least one electrode is implanted within the spinal column of the patient at a T4-T6 spinal nerve level, and wherein the ailment is lower back pain.

2. The method of claim 1, wherein the at least one electrode is implanted within the spinal column of the patient at a T5 spinal nerve level.

3. The method of claim 1, wherein stimulation of the neural structure is prevented.

4. The method of claim 1, wherein the neural structure is a dorsal root (DR) nerve fiber.

5. The method of claim 1, wherein the activation threshold of the neural structure relative to the activation threshold of the DC nerve fiber is increased by applying electrical suppression energy to the neural structure.

6. The method of claim 5, wherein the electrical stimulation energy is applied to DC nerve fiber by sinking electrical current at a first one of the at least one electrode adjacent the DC nerve fiber, thereby treating the ailment, and the electrical suppression energy is applied to the neural structure by sourcing at least a portion of the electrical current from a second one of the at least electrode adjacent the neural structure, thereby increasing the activation threshold of the neural structure.

7. The method of claim 6, further comprising sinking at least a portion of the electrical current sourced at the second electrode into a remote electrode.

8. The method of claim 6, wherein electrical suppression energy is applied to another neural structure adjacent the DC nerve fiber to increase the activation threshold of the other neural structure by sourcing at least another portion of the electrical current from a third one of the at least one electrode adjacent the other neural structure, wherein the electrical stimulation energy is applied to the DC nerve fiber while the activation threshold of the other neural structure is increased, thereby treating the ailment while minimizing stimulation of the other neural structure.

9. The method of claim 8, wherein neural structure is a first dorsal root (DR) nerve fiber, and the other neural structure is a second dorsal root (DR) nerve fiber.

10. The method of claim 8, wherein the first electrode is a center electrode, and the second and third electrodes are flanking electrodes of a tripole configuration located between the neural structures.

11. The method of claim 5, wherein the activation threshold of the neural structure is increased by applying a sub-threshold, hyperpolarizing conditioning pre-pulse to the neural structure, and electrical stimulation energy is applied to the DC nerve fiber by applying a depolarizing stimulation pulse to the DC nerve fiber.

12. The method of claim 11, wherein the conditioning pre-pulse has a duration less than 200 µs.

13. The method of claim 5, wherein the activation threshold of the neural structure is increased by applying electrical background energy to the neural structure in accordance with at least one stochastic parameter to the neural structure.

14. The method of claim 13, wherein the electrical background energy comprises pulses, and the at least one stochastic parameter comprises at least one of an interpulse interval, pulse amplitude, pulse shape, and pulse duration.

15. The method of claim 13, wherein the electrical background energy comprises white noise, and the at least one stochastic parameter comprises a frequency.

* * * * *